United States Patent
Ramsing et al.

(10) Patent No.: US 11,124,764 B2
(45) Date of Patent: Sep. 21, 2021

(54) INCUBATOR APPARATUS AND METHODS

(71) Applicant: UNISENSE FERTILITECH A/S, Aarhus N (DK)

(72) Inventors: Niels Ramsing, Aarhus (DK); Jonas Lerche Hansen, Aarhus (DK); Kim Bondergaard Madsen, Aarhus (DK); Troels Kofoed Mejer, Aarhus (DK); Jorgen Berntsen, Viborg (DK)

(73) Assignee: UNISENSE FERTILITECH A/S, Aarhus N (DK)

( * ) Notice: Subject to any disclaimer, the term of this patent is extended or adjusted under 35 U.S.C. 154(b) by 35 days.

(21) Appl. No.: 15/116,204

(22) PCT Filed: Jan. 13, 2015

(86) PCT No.: PCT/EP2015/050466
§ 371 (c)(1),
(2) Date: Aug. 2, 2016

(87) PCT Pub. No.: WO2015/113810
PCT Pub. Date: Aug. 6, 2015

(65) Prior Publication Data
US 2017/0009202 A1    Jan. 12, 2017

(30) Foreign Application Priority Data
Feb. 3, 2014    (GB) .................................. 1401773

(51) Int. Cl.
*C12N 5/073*    (2010.01)
*C12M 1/00*    (2006.01)
(Continued)

(52) U.S. Cl.
CPC ........... *C12N 5/0604* (2013.01); *C12M 21/06* (2013.01); *C12M 23/50* (2013.01); *C12M 25/00* (2013.01);
(Continued)

(58) Field of Classification Search
CPC ...... C12M 21/06; C12M 23/50; C12M 41/14; C12M 41/36; C12M 25/00; C12M 41/46; C12M 41/48; C12N 5/0604
See application file for complete search history.

(56) References Cited

U.S. PATENT DOCUMENTS

| 4,800,164 A | 1/1989 | Bisconte |
| 2006/0141609 A1 | 6/2006 | Kagayama et al. |

(Continued)

FOREIGN PATENT DOCUMENTS

| EP | 0171319 A1 | 2/1986 |
| EP | 0239450 A1 | 9/1987 |

(Continued)

OTHER PUBLICATIONS

International Search Report dated Mar. 18, 2015, issued in International Application No. PCT/EP2015/050466.
(Continued)

*Primary Examiner* — Gautam Prakash
(74) *Attorney, Agent, or Firm* — Honigman LLP

(57) ABSTRACT

Apparatus and methods for monitoring embryos in an incubator are described. The apparatus comprises an incubation chamber defined by an incubation chamber housing and a sample platform comprising a plurality of receptacles for holding embryos within the incubation chamber for incubation. The sample platform may comprise a slide carrier on which embryo slides containing the receptacles may be placed incubation. The sample platform is rotatable about a rotation axis relative to the incubation chamber housing so as to allow receptacles to be selectively rotated to a monitoring position that is aligned with a viewing port provided in the incubation chamber housing, for example an opening or window. An imaging device is located outside the incubation chamber and arranged to image embryos within the
(Continued)

incubation chamber at the monitoring position through the viewing port.

15 Claims, 4 Drawing Sheets

(51) Int. Cl.
  *C12M 3/00*   (2006.01)
  *C12M 1/34*   (2006.01)
  *C12M 1/12*   (2006.01)
  *C12M 1/36*   (2006.01)

(52) U.S. Cl.
  CPC ............ *C12M 41/14* (2013.01); *C12M 41/36* (2013.01); *C12M 41/46* (2013.01); *C12M 41/48* (2013.01)

(56) References Cited

U.S. PATENT DOCUMENTS

2009/0130750 A1  5/2009  Ceechi
2010/0151564 A1  6/2010  Beebe et al.
2011/0205351 A1  8/2011  Nakamura et al.

FOREIGN PATENT DOCUMENTS

| WO | 02/33047 A2 | 4/2002 | |
|---|---|---|---|
| WO | 2004/003131 A2 | 1/2004 | |
| WO | WO-2004003131 A2 * | 1/2004 | ............... A01N 1/02 |
| WO | 2010/056755 A2 | 5/2010 | |

OTHER PUBLICATIONS

UK Combined Search and Examination Report dated Oct. 22, 2014, issued in UK Application No. GB1401773.5.

Written Opinion of the International Searching Authority dated Mar. 18, 2015, issued in International Application No. PCT/EP2015/050466.

Notification Concerning Transmittal of International Preliminary Report on Patentability (Chapter I of the Patent Cooperation Treaty) dated Aug. 18, 2016, issued in International Application No. PCT/EP2015/050466.

* cited by examiner

INCUBATOR APPARATUS AND METHODS

This application claims the benefit under 35 USC 371 to International Application No. PCT/EP2015/050466, filed Jan. 13, 2015, which claims priority to GB Patent Application No. 1401773.5, filed Feb. 3, 2014, each of which is incorporated by reference in its entirety.

BACKGROUND OF THE INVENTION

The present invention relates to incubator apparatus and methods.

Infertility affects more than 80 million people worldwide. It is estimated that 10% of all couples experience primary or secondary infertility. In vitro fertilization (IVF) is an elective medical treatment that may provide a couple who has been otherwise unable to conceive a chance to establish a pregnancy. It is a process in which eggs (oocytes) are taken from a woman's ovaries and then fertilized with sperm in the laboratory. The embryos created in this process are then placed into the uterus for potential implantation. In between fertilization (insemination) and transfer the embryos are typically stored in an incubation chamber of an incubator for 2-6 days during which time they may be regularly monitored, for example through imaging, to assess their development. Conditions within the incubator, such as temperature and atmospheric composition, are controlled, generally with a view to emulating the conditions in the oviduct and uterus. Thus, when incubating embryos it can be important to seek to maintain a stable environment, e.g. in terms of temperature and/or atmosphere, within the incubation chamber.

In a typical IVF cycle a number of eggs from a single patient will be fertilised and the resulting embryos incubated. However, it is usual for not all incubated embryos to be transferred to the patient's uterus. This is to reduce the risk of potentially dangerous multiple births. Embryos will typically be selected for transfer on the basis of an assessment of the development potential of the embryos that have been incubated. Embryos determined to have the greatest potential for developing into a live birth will be preferentially selected over other embryos in their cohort. Accordingly, an important aspect of IVF treatment is assessing development potential of the embryos comprising a cohort, i.e. determining embryo quality where embryo quality is a prediction representing the likelihood of an embryo successfully implanting, developing in the uterus after transfer and leading to the birth of a healthy baby.

A powerful tool for assessing embryo quality that has recently been developed is time-lapse embryo imaging. Time-lapse embryo imaging involves obtaining images of embryos during their development. This can allow the timings of various developmental events, such as cell divisions, to be established. These timings may sometimes be referred to as morphokinetic parameters for the embryo. Studies have shown how the timings and durations of various embryonic development events can be correlated with development potential for an embryo. For example, a relatively early time of division from one cell to two cells has been found to be an indicator of a good quality embryo. Other morphokinetic parameters, for example the degree of synchronicity in the two divisions when dividing from two cells to four cells, are also found to be sensitive to embryo quality.

With time-lapse embryo imaging (time-lapse microscopy) becoming an established technique for monitoring embryos in order to assess embryo quality, apparatus developed specifically for performing time-lapse embryo imaging have become available.

One well-known apparatus for performing time-lapse embryo imaging is the EMBRYOSCOPE (RTM) device and associated EMBRYO VIEWER (RTM) software developed by, and available from, Unisense FertiliTech A/S (Aarhus, Denmark). The EMBRYOSCOPE (RTM) apparatus has the ability to incubate embryos on six removable slides supported by a slide carrier. Each slide comprises a 3×4 array of receptacles and so is able to hold up to 12 embryos with each embryo in a separate receptacle in its own media droplet separate from the others. In principle this provides the apparatus with a 72-embryo capacity. However, in practical use, each slide is only used for embryos from a single patient and as not all treatments involve exactly 12 embryos typically not all receptacles for every slide will be used. The EMBRYOSCOPE (RTM) apparatus has a built-in microscope for imaging the embryos. The slide carrier is movable relative to the microscope in two horizontal directions (x- and y-directions) to allow embryos in different receptacles to be sequentially moved into the field of view of the microscope for imaging. Embryos are imaged one-at-a-time and the walls of the receptacles are arranged to reduce the risk of an embryo transferring from one receptacle to another during incubation. The microscope is further configured to image the embryos with its focal plane at a plurality of different heights (z-direction). The use of the EMBRYOSCOPE (RTM) apparatus has changed over time as the original apparatus was developed primarily for academic purposes and the apparatus is now widely used for routine IVF. This means that while the EMBRYOSCOPE (RTM) apparatus provides excellent performance with a large amount of flexibility in operation, there are some aspects to the design which are perhaps in some respects less optimised for what has now become a more mainstream device. For example, there are some aspects to the design, such as the provision of relative movement in two orthogonal directions, which increases the cost of manufacture. Furthermore, as time-lapse embryo imaging is becoming a more and more established technique it can be expected there will be a desire to provide more compact apparatus with greater capacities than are currently available.

A number of other devices for performing time-lapse embryo imaging have been proposed, for example the EMBRYOGUARD apparatus from IMT International Limited, the IVF Embryo Observation System CCM-IVF from Astec Co. Limited, and the Live Cell Imaging Incubation System from Sanyo E&E Europe BV. However, these devices have various drawbacks. For example, using relatively large incubation chambers with various components of the apparatus operating therein, which can make the conditions in the incubation chambers more difficult to control. For example, temperature gradients and unintentional heating caused by positioning motors, degassing of embryotoxic compounds by printed circuit boards and plastics, and so on, can all impair embryo development.

There is therefore a need for new designs of apparatus for monitoring embryos during incubation which can help to address some of these issues with existing designs.

SUMMARY OF THE INVENTION

According to a first aspect of the invention there is provided an apparatus for monitoring embryos during incubation; the apparatus comprising: an incubation chamber defined by an incubation chamber housing; a sample platform comprising a plurality of receptacles for holding embryos within the incubation chamber for incubation, wherein the sample platform is rotatable about a rotation axis relative to the incubation chamber housing to allow embryos to be selectively rotated to a monitoring position aligned with a viewing port in the incubation chamber housing; and an imaging device located outside the incubation chamber and arranged to image embryos within the incubation chamber at the monitoring position through the viewing port.

In accordance with some embodiments the plurality of receptacles comprise a group of receptacles arranged to hold embryos at locations on an arc of a circle centred on the rotation axis.

In accordance with some embodiments the plurality of receptacles comprise groups of receptacles arranged to hold embryos at locations on arcs of a plurality of circles centred on the rotation axis with different radii.

In accordance with some embodiments an imaging axis of the imaging device is moveable along a radial direction extending from the rotation axis to allow the imaging axis to be aligned with respective ones of the plurality of circles centred on the rotation axis with different radii.

In accordance with some embodiments the imaging device comprises imaging components arranged on opposite sides of the incubation chamber.

In accordance with some embodiments the imaging device comprises a microscope.

In accordance with some embodiments the apparatus further comprises a motor for driving the rotation of the sample platform relative to the incubation chamber housing.

In accordance with some embodiments the apparatus further comprises a controller adapted to control the motor to rotate a selected receptacle to the monitoring position.

In accordance with some embodiments the controller is further adapted to select a receptacle to be moved to the monitoring position in accordance with a predefined monitoring programme for embryos in the receptacles.

In accordance with some embodiments the sample platform comprises a slide carrier with a plurality of removable embryo slides containing the receptacles mounted thereon.

In accordance with some embodiments the slide carrier comprises a plurality of compartments for receiving embryo slides at locations corresponding to sectors around an arc of a circle centred on the rotation axis.

In accordance with some embodiments adjacent compartments are on either side of compartment walls extending in a radial direction away from the rotation axis.

In accordance with some embodiments the apparatus further comprises a temperature control system arranged to control a temperature of the sample platform.

In accordance with some embodiments the apparatus further comprises an environment control system arranged to control environmental conditions within the incubation chamber.

In accordance with some embodiments the apparatus further comprises further monitoring equipment for monitoring an aspect of embryos in the incubation chamber, wherein the further monitoring equipment is positioned such that the sample platform is rotatable about the rotation axis relative to the incubation chamber housing to allow embryos to be selectively rotated to a further monitoring position for monitoring by the further monitoring equipment.

In accordance with some embodiments the sample platform is generally in the form of a circular disc.

According to a further aspect of the invention there is provided an embryo slide for use in an apparatus according to any preceding claim, wherein the embryo slide comprises a substrate with a plurality of receptacles provided therein, and wherein the receptacles are arranged at locations along an arc of a circle.

According to a further aspect of the invention there is provided a method of monitoring embryos during incubation; the method comprising: providing an incubation chamber defined by an incubation chamber housing; providing a sample platform comprising a plurality of receptacles for holding embryos within the incubation chamber for incubation; providing an imaging device located outside the incubation chamber and arranged to image embryos within the incubation chamber at a monitoring position aligned with a viewing port in the incubation chamber housing; rotating the sample platform about a rotation axis relative to the incubation chamber housing to rotate a selected embryo to the monitoring position; and imaging the selected embryo through the viewing port using the imaging device.

It will be appreciated that features and aspects of the invention described above in relation to the first and other aspects of the invention are equally applicable to, and may be combined with, embodiments of the invention according to other aspects of the invention as appropriate, and not just in the specific combinations described above.

BRIEF DESCRIPTION OF THE DRAWINGS

The invention is now described by way of example only with reference to the following drawings in which.

DETAILED DESCRIPTION

Figure 1:
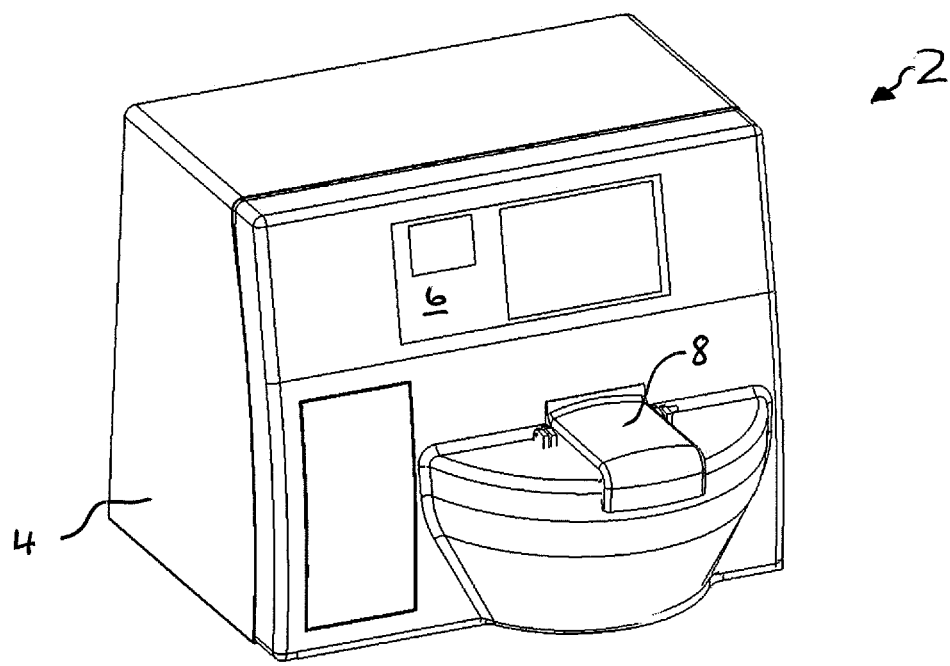
FIG. 1 schematically represents an incubator apparatus in accordance with an embodiment of the invention.

FIG. 1 schematically represents in perspective view an incubator apparatus 2 in accordance with an embodiment of the invention. It will be appreciated that all features and operational aspects of the apparatus 2 which are not described in detail herein may be implemented in accordance with known techniques, for example in accordance with the principles used in previous time-lapse embryo imaging apparatus, such as those discussed above, and other incubators.

The apparatus 2 in this example has a characteristic footprint on the order of 60 cm×50 cm and a height that is on the order of 50 cm. The apparatus 2 comprises an outer casing 4 which houses two touch-sensitive displays providing a user interface 6 through which a user can interact with the apparatus 2, e.g. to provide control commands and read status information. The outer casing 4 includes a pivotable loading port cover 8 that is discussed further below.

Figure 2:
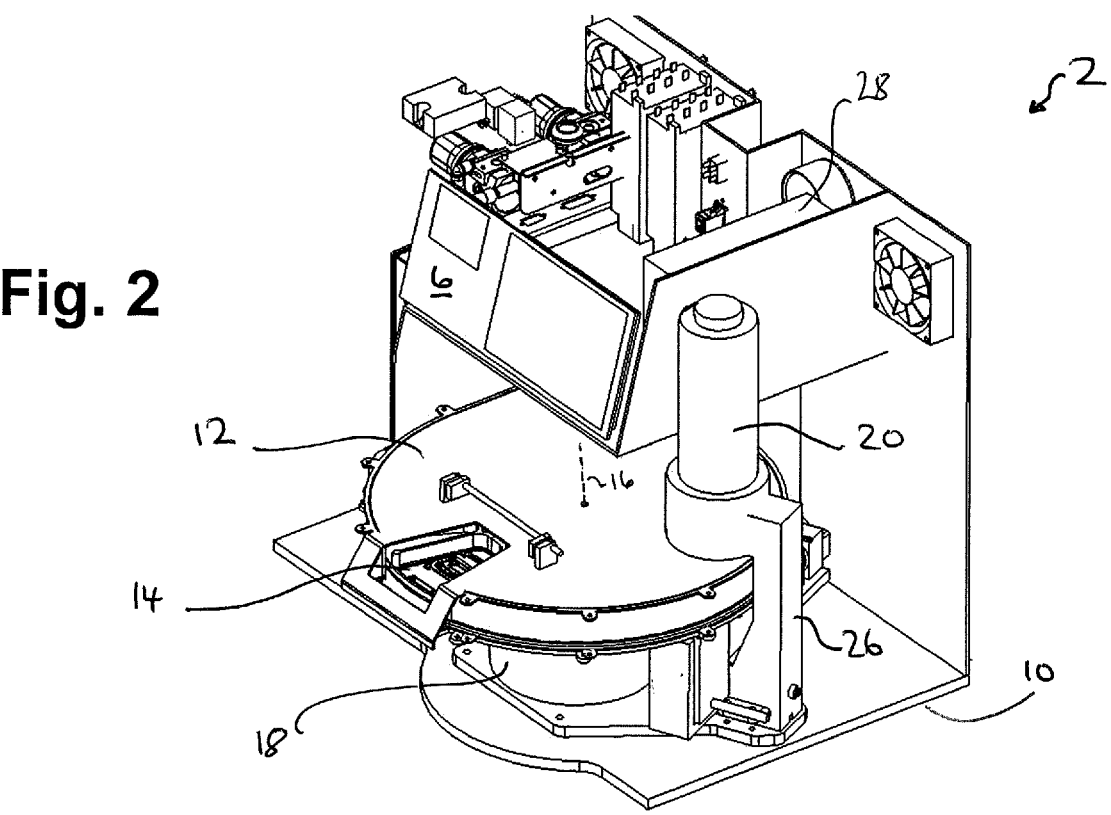
FIG. 2 schematically represents the incubator apparatus of FIG. 1 with an outer casing removed.

FIG. 2 schematically represents the incubator apparatus 2 of FIG. 1 from a different viewpoint and with the outer casing 4 removed to reveal various internal components of the apparatus 2. The apparatus 2 comprises a base plate 10 to which various other components are mounted. At its heart the incubator 2 includes an incubation chamber defined by an incubation chamber housing 12 and a slide carrier 14. The slide carrier comprises a plurality of compartments for holding respective embryo slides having receptacles for embryos to be incubated within the incubation chamber (only a small part of the slide carrier is visible in FIG. 2). The various aspects of the apparatus 2 may be made from any suitable materials. For example, in one implementation the incubator chamber housing 12 may be formed from sheet steel, the slide carrier 14 may be formed from aluminium, and the embryo slides (not shown in FIGS. 1 and 2) may be formed from moulded plastic.

The apparatus 2 further comprises an imaging device 20, in this case a digital microscope. The microscope 20 is mounted outside the incubation chamber in alignment with a viewing port in the incubation chamber housing 12 to allow the microscope to record images of embryos in the incubation chamber. The imaging device 20 comprises an illumination component with condenser optics located on one side of the incubation chamber (below the incubation chamber and not visible in the view represented in FIG. 2) and an imaging optics and sensor component located on an opposite side of the incubation chamber (above the incubation chamber for the orientation represented in FIG. 2). These two components of the imaging device are connected by a mounting arm 26 to help ensure proper alignment between them. It will be appreciated alternative configurations for the imaging device may be adopted in accordance with other embodiments. For example, the imaging optics and sensor could be arranged below the incubation chamber (embryo chamber) with the illumination component above, or, in another example, the imaging and illumination components may be on the same side (above or below) of the incubation chamber, for example using a ring illuminator placed around an objective lens for dark field illumination, back scattered light or fluorescent light imaging. The imaging device 20 and its operation in obtaining time-lapse embryo imaging data may follow broadly conventional techniques. For example, the imaging device 20 may be similar to that used in the known EMBRYOSCOPE (RTM) apparatus discussed above. For example, the imaging device 20 may employ a 20×N.A. 0.40 LWD (long working distance) Hoffman modulation contrast objective coupled to a 2048×1088 pixel (with 3 pixels per μm) monochrome 12-bit sensor with illumination from a 1W red LED (with peak emission around 635 30 nm). Likewise, the operational aspects of the apparatus relating to image data acquisition and storage may follow generally conventional techniques.

The incubation chamber housing 12 and the slide carrier 14 are both generally circular and relatively thin (i.e. disc like)—for example with a thickness (height) of less than an amount selected from the group comprising 5 cm, 4 cm, 3 cm, 2 cm and 1 cm for the slide carrier and less than an amount selected from the group comprising 10 cm, 9 cm, 8 cm, 7 cm, 6 cm, 5 cm, 4 cm, 3 cm, 2 cm and 1 cm for the incubation chamber housing. The characteristic width (diameter) of the incubation chamber housing may, for example, be in range selected from the group comprising larger than 15 cm and less than 60; larger than 25 cm and less than 50 cm; larger than 30 cm and less than 40 cm. Thus the incubation chamber's characteristic extent in a first direction (diameter/width) may be greater than the incubation chamber's characteristic extent in a second direction (height/thickness) by a factor that is greater than 2, for example greater than 3, for example greater than 5, for example greater than 10.

The incubation chamber housing 12 is fixed in position relative to the base plate 10. The slide carrier 14 is rotatable within the incubation chamber defined by the incubation chamber housing 12 about a rotation axis 16. In this example the slide carrier 14 is mounted directly to a shaft of a motor 18 mounted below, and outside, the incubation chamber. Thus the shaft of the motor 18 passes through an opening in the underside of the incubation chamber and is coupled to the slide carrier such that the motor can drive the slide carrier to rotate within the incubation chamber. Other configurations of motor can be employed to drive the slide carrier to rotate within the incubation chamber in accordance any established motor drive techniques, for example motor configurations without a central shaft and using a liner motor coupled to the perimeter of a hollow tube to which the slide carrier is mounted may be used. Thus different embryos within the incubation chamber may be rotated into alignment with the imaging device for monitoring (image acquisition). In some examples the slide carrier 14 might be indirectly driven by the motor through a system of gears/belts. However, in such cases it may be appropriate to take steps to ensure slack in the drive system does not impact the extent to which the embryos can be reliably and repeatedly aligned with an imaging axis of the imaging device 20.

Other components of the apparatus 2 include a power supply, a gas control system for controlling conditions within the incubation chamber, for example in terms of temperature and composition of the atmosphere. An interface through which time-lapse embryo imaging data may be exported and/or control instructions and configuration information may be imported may also be included in some embodiments. The apparatus further includes a central control unit 28, for example based around a programmable computer running an appropriate control program, to control the operation of the apparatus. The central control unit may provide various control functions, for example in terms of controlling the imaging device 20 to acquire embryo image data and to provide storage of the image data, to control the rotation of the slide carrier 14, to control the gas control system, the user interface 6, and so forth. In some examples the control unit 28 may also support analysis functions for determining embryo quality and providing an indication thereof to a user. In some examples a single control unit may provide these functions whereas in other examples separate control units may be provided for some functions. For example, a separate control unit may be provided for the gas control system to help ensure the gas control system continues to operate to maintain desirable incubation conditions for embryos in the event of a failure of another aspects of the control system. Since these other components of the incubator apparatus may be based on conventional techniques they are not described here in detail in the interest of brevity. That is to say, except as where described otherwise herein, all other design and operational aspects of the apparatus 2 may be based on existing techniques. For example, the apparatus 2 may employ a gas control system similar to that used in the known EMBRYOSCOPE (RTM) apparatus discussed above. For example, the gas control system may be a tri-gas system providing gas temperature stabilisation to within ±0.2° C. in the range 30° C. to 45° C. and Oxygen concentration stabilisation to within ±0.2% in the range 10 5% to 20% and Carbon Dioxide concentration stabilisation to within ±0.2% in the range 2% to 10%. The gas control system may further provide regular purification/regeneration of the gas volume within the incubation chamber. The recirculation path may include filters such as an active carbon filter for volatile organic compounds and a HEPA filter for particles.

Figure 3:
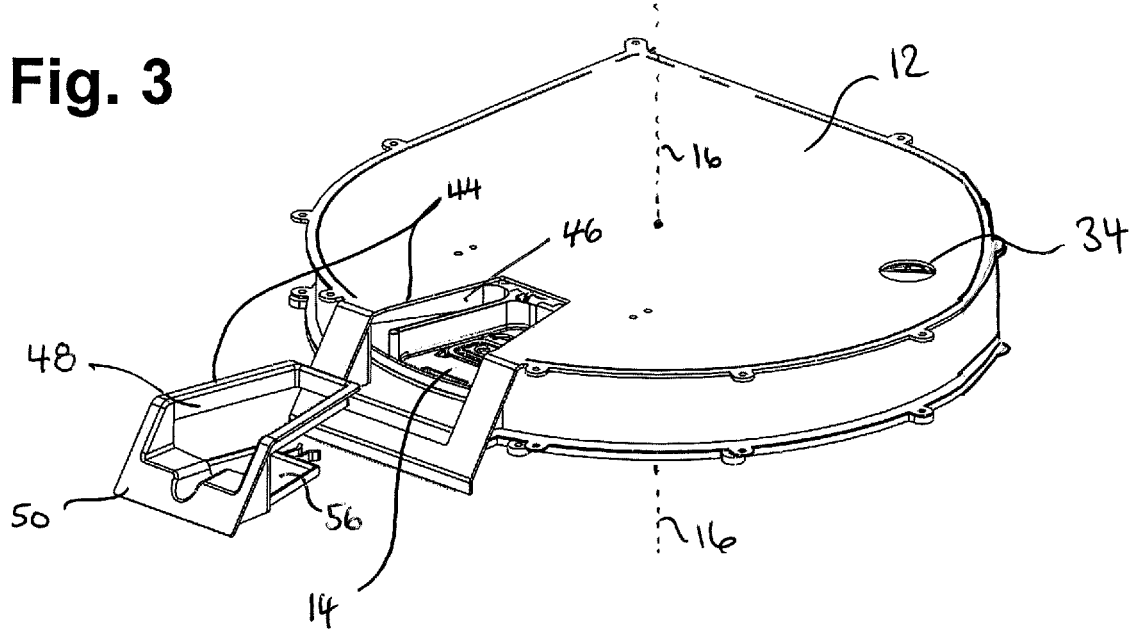
FIG. 3 schematically represents an incubation chamber housing and associated loading port insert and slide carrier of the incubator apparatus of FIGS. 1 and 2.
Figure 4:
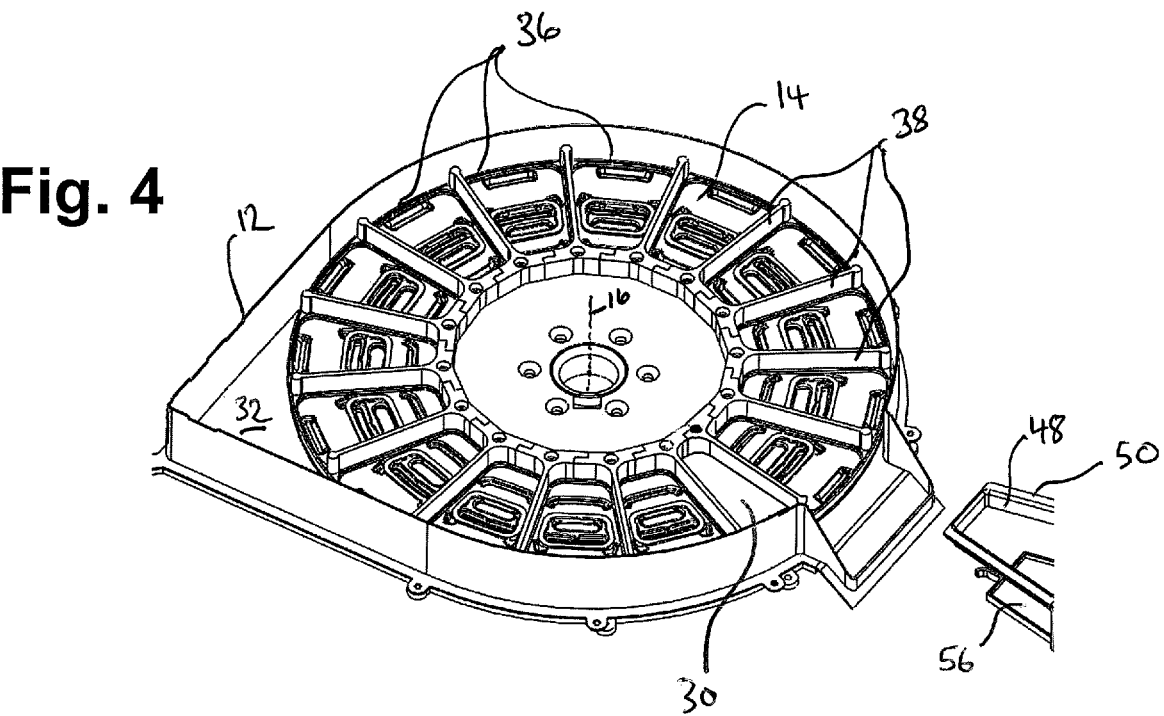
FIG. 4 schematically represents the incubation chamber housing of FIG. 3 with the lid removed to reveal more detail of the slide carrier.

FIGS. 3 and 4 are perspective views (from different viewpoints) schematically showing the incubation chamber housing 12 and slide carrier 14 of the incubation chamber of the apparatus 2 represented in FIGS. 1 and 2 in more detail. FIG. 4 differs from FIG. 3 in representing the incubation chamber with a lid part of the incubation chamber housing 12 removed to expose more details of the slide carrier 14.

As noted above, the incubation chamber is generally disc like, although in this particular example embodiment one quadrant of the incubation chamber housing 12 is extended into a corner while the slide carrier 14 maintains a more circular shape. This gives rise to a gas-exchange region 32 within the incubation chamber that is spaced away from embryos on the slide carrier 14 to provide a region where gas may be introduced to and removed from the incubation chamber by the external gas control system to reduce the impact of gas flows on the embryos within the incubation chamber. This region may also be used for sensors and gas sampling ports associated with the atmospheric control of the incubation chamber, for example redundant sensors and gas sampling ports provided in addition to sensors and gas sampling ports provided elsewhere. More generally a gas-exchange region may be established by providing a region of the incubation chamber housing 12 which extends away from the slide carrier to define the gas exchange region, and this need not follow the specific corner-like design represented in FIGS. 3 and 4.

Apparent in FIG. 3 is the viewing port 34 discussed above, but which is not apparent in FIG. 2 because it is obscured by the imaging device 20 in that figure. The viewing port 34 comprises a transparent region in the incubation chamber housing 12 through which the imaging device 20 can image embryos within the incubation chamber. The viewing port 34 may comprise a simple opening or may include a window. The window may be plain, or comprise a part of the optical system of the imaging device 20. Where the viewing port comprises a simple opening the imaging device 20 may be close coupled to the incubation chamber housing 12 to restrict the extent to which the incubation chamber is not sealed in this region. In this particular example implementation in which the imaging device 20 includes an illumination component 24 below the incubation chamber, there is a corresponding opening in the underside of the incubation chamber housing through which the illumination light may pass. As noted above, in some other examples the imaging optics/sensor may be on the bottom side of the incubator, and in such cases the viewing port through which the embryos are imaged will correspondingly be on the bottom side of the incubator housing. In this case the illumination may be provided from above the incubator (through a corresponding opening/window on the upper side of the incubation chamber housing). In either case, and as noted above, in some configurations the illumination source and the imaging optics and sensor may be on the same side of the incubation chamber, for example for back scattered-light, dark-field or fluorescence imaging.

As can be seen in FIG. 4 the slide carrier 14 comprises a plurality of compartments 36 generally arranged as sectors around a circle centred on the rotation axis 16. In this particular example there are fifteen compartments comprising the slide carrier. The slide carrier 14 further includes a sensor region 30 between two of the compartments 36. This provides a location at which monitoring equipment, for example a temperature sensor and/or a pH sensor, may be mounted. One particular type of pH sensor which could conveniently be used is an optic pH sensor, for example a SAFE Sens IVM type sensor available from Blood Cell Storage, Inc. USA, for providing a fluorescence signal based indication of pH. Sensors for other parameters relevant to incubator control can also be mounted on the sample carrier as appropriate. In some examples there may be multiple sensor regions provided at different location on the sample carrier, for example between various other pairs of compartments 36 or at other locations to provide more positions for such sensing (e.g. to provide redundancy).

The respective compartments are defined by compartment walls 38. The compartment walls 38 separating adjacent compartments 36 comprise radial portions extending radially outwards from the rotation axis 16 to the outer periphery of the slide carrier 14. In this example the compartment wall 38 for each compartment 36 further comprises an inner azimuthal portion connecting between the ends of the radial portions of the compartment wall which are nearest to the rotation axis 16. Thus the respective compartments 36 are surrounded on three sides by their respective compartment walls 38. In principle the slide carrier 14 with its compartment walls 38 could be machined from a single block of material, but in this example the slide carrier comprises a substantially planar base portion with the compartment walls 38 attached thereto in a modular fashion, as schematically represented in the figure.

Although not visible in the figures, the slide carrier 14 in accordance with embodiments of the invention is provided with a heating element as part of a temperature control system of the apparatus that is configured to control the temperature of the slide carrier, and hence the embryos mounted thereon, in accordance with desired incubation conditions. The heating element may, for example, comprise a heating foil and temperature sensor attached to the sample carrier 14 in the sensor region 30 (or any other suitable location) and connected to a temperature control circuit, for example based on conventional temperature servo-control techniques.

Each compartment 36 is configured to receive and hold a removable embryo slide having receptacles for receiving embryos for incubation thereon. The use of removable embryo slides provides for easy transportation of embryos to and from the apparatus before and after incubation, and furthermore helps to avoid cross contamination. Typically the embryo slides will be disposable ("one-time-use") with individual slides being used for embryos from a single patient. A combination of the slide carrier with embryo slides mounted thereon may conveniently be referred to as a sample platform.

Figure 5:
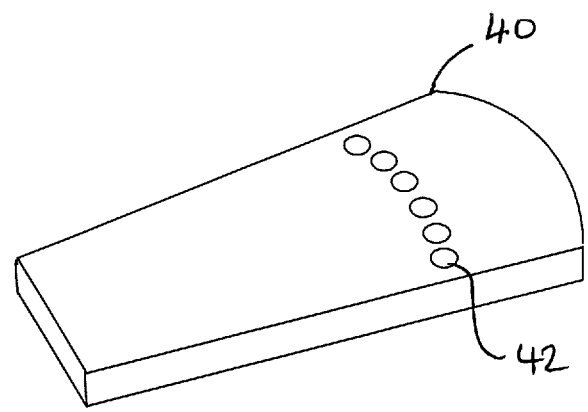
FIG. 5 schematically represents a sample slide containing receptacles for holding embryos in accordance with an embodiment of the invention.

FIG. 5 is a schematic perspective view of an embryo slide 40 for use in the incubator apparatus 2. The embryo slide 40 in this example is plastic and formed by injection moulding. The dimensions of the embryo slide 40 and any profiling on its lower surface are arranged to cooperate with the dimensions and shape of the compartments of the slide carrier 14. Thus the embryo slide 40 may be loaded into one of the compartments 36 of the slide carrier 14 to hold it during incubation. The embryo slide 40 comprises a plurality of receptacles 42 for holding embryos to be incubated. There are six receptacles shown for the slide 40 represented in FIG. 5, but there may typically be more than this. For example there may be 16 receptacles on a slide. Each receptacle 42 may have a size and shape corresponding to any known design for receptacles for embryos for incubation. The locations of the receptacles 42 are arranged so as to hold embryos along a curved line corresponding to an arc of a circle centred on the slide carrier's rotation axis 16 when the embryo slide is loaded into a compartment of the slide carrier. Furthermore, the locations of the receptacles are arranged so that when an embryo slide is loaded into the slide carrier the receptacles hold embryos at a distance from the rotation axis 16 which corresponds to a distance from the rotation axis 16 of the viewing port 34 in the incubation chamber housing 12 and an imaging axis of the imaging device 20. This means that individual receptacles of the different embryo slides can be brought into alignment with the imaging axis of the imaging device 20 simply by rotating the slide carrier relative to the incubation chamber housing to an appropriate position, which may be referred to as a monitoring position for a selected embryo. The rotation of the slide carrier 14 to place the embryo to be imaged in the monitoring position can be controlled by driving the motor 18 in accordance with conventional motor control techniques, for example using an encoder to track the position of the slide carrier 14 relative to the incubation chamber housing 12 as it is rotated. When a receptacle containing an embryo selected for monitoring is rotated to the monitoring position it may be imaged using the imaging device, and the corresponding image data stored for later analysis in accordance with conventional time-lapse embryo imaging techniques.

Thus, embryos in the incubation chamber can be sequentially brought into alignment with the imaging device for monitoring (image acquisition) by simply rotating the slide carrier 14 to an appropriate position. The frequency and timing at which the respective embryos are imaged can be performed in accordance with a desired monitoring programme. In particular, the control unit 28 which is configured to govern the operation of the apparatus 2 may be adapted to control the rotation of the slide carrier 14 and the operation of the imaging device 20 to acquire images according to a desired monitoring programme. The specific monitoring programme to be used in a given implantation is not significant to the principles underlying the embodiments of the invention described herein.

As can be seen in FIG. 3 the incubation chamber housing 12 generally comprises a flat lower surface and a flat upper surface separated by a side wall. In use the majority of compartments 36 comprising the slide carrier 14 are within the incubation chamber defined by the incubation chamber housing 12 and so not readily accessible for loading and/or unloading of embryo slides. Thus, a loading port 44 is provided in association with the incubation chamber housing 12 to allow embryo slides to be individually loaded into whichever compartment is in a loading position, i.e. aligned with the loading port 44. Accordingly, different ones of the compartments can be moved to the loading position for loading/unloading of an embryo slide that is to be placed in or removed from the incubation chamber. A selected compartment can be moved to the loading position by appropriate rotation of the slide carrier relative to the incubation chamber housing using the motor 18. Thus, in a slide loading operation the control unit 28 may be configured to move a compartment in which a slide is to be loaded to the loading position aligned with the loading port 44. Similarly, in a slide unloading operation the control unit 28 may be configured to move a particular compartment from which a slide is to be uploaded to align with the loading position (in this regard the loading position may also be referred to as an unloading position). The specific times at which particular embryo slides are loaded into and removed from compartments may be selected according to the application at hand, for example in accordance with a desired incubation programme in terms of time and duration of incubation. An indication of the identity of the compartment currently in the loading position may be provided on the user interface 6 and a user may select a compartment to be brought to the loading position using the user interface 6.

The loading port 44 is defined by a loading port opening 46 (based around a cut out in the incubation chamber housing 12) and a loading port wall 48. In some examples the loading port wall may be integrally formed with the incubation chamber housing 12, but in this example the loading port wall 48 is provided by a separate loading port insert 50. The loading port insert 50 is shown separated from the incubation chamber housing 12 in FIGS. 3 and 4 for ease of representation. However, in use the loading port insert 50 is placed in position in the associated cut out in the incubation chamber housing 12 where it is retained, for example by clips or other fixings.

The loading port insert 50 in this example includes a spillage tray 56 arranged generally beneath the opening defined by the loading port walls 48. The loading port insert 50 is arranged so that when coupled to the incubation chamber housing 12, the spillage tray 56 is positioned beneath the sample carrier, and in particular beneath a compartment in the loading position. The compartments 36 of the slide carrier 14 will in general have openings (holes) which align with the positions of embryos to allow imaging. For example, where the embryos are illuminated from below, the holes allow illumination light to pass through the sample carrier and where the embryos are imaged from below, the holes allow the embryos to be viewed through the sample carrier (if the embryos are illuminated and imaged from above, there might be no holes). If there are holes in the bottom of the compartments, it is possible that fluids accidentally spilt from a slide during loading or unloading (e.g. growth media or oil) or introduced during cleaning (e.g. cleaning fluid) can pass through the sample carrier and into the interior of the incubation chamber. If this happens, the spilt liquid can be expected to drop into the spillage tray 56 arranged beneath the compartment in the loading position. The loading port insert 50 can then readily be removed for cleaning or replacement. This can be much simpler than disassembling the incubation chamber for internal cleaning which might otherwise be required after a spillage.

The loading port opening 46 is sized to allow an embryo slide to pass through the opening 46 for placing in (or unloading from) a compartment 36 of the sample carrier 14 which has been moved to the loading position aligned with the loading port 44. Once a slide (tray) has been loaded in or unloaded from the selected compartment in the loading position, the incubation apparatus may proceed to move another compartment into alignment with the loading port to allow another slide to be loaded/unloaded. Alternatively, the incubator apparatus may proceed with monitoring embryos in the incubation chamber by rotating the relevant receptacles to the monitoring position associated with the viewing port 34/imaging device 20. The specific operation in this regard will depend on the incubation programme being undertaken.

Figure 6:
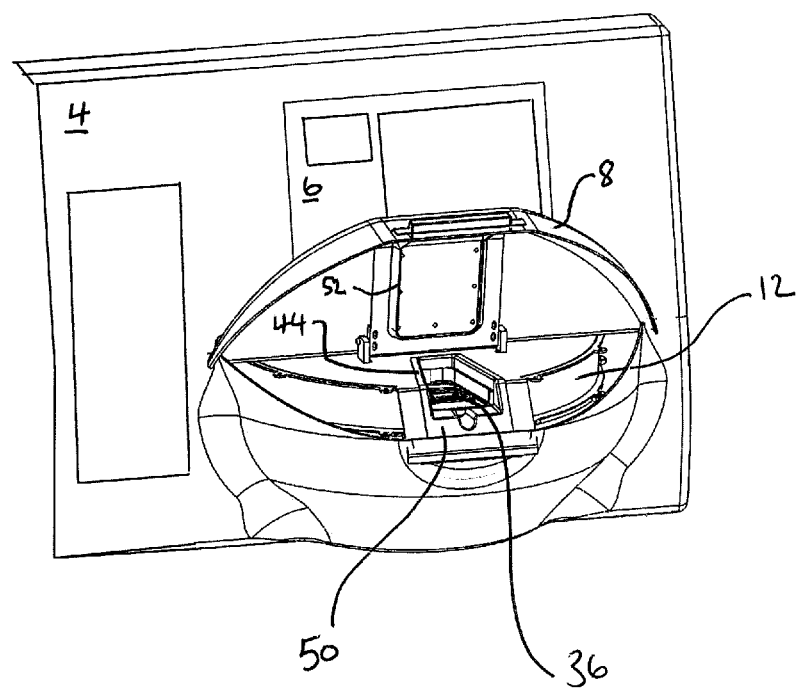
FIG. 6 schematically represents a front face of the incubator apparatus of FIG. 1 with a loading port cover in an open position.
Figure 7:
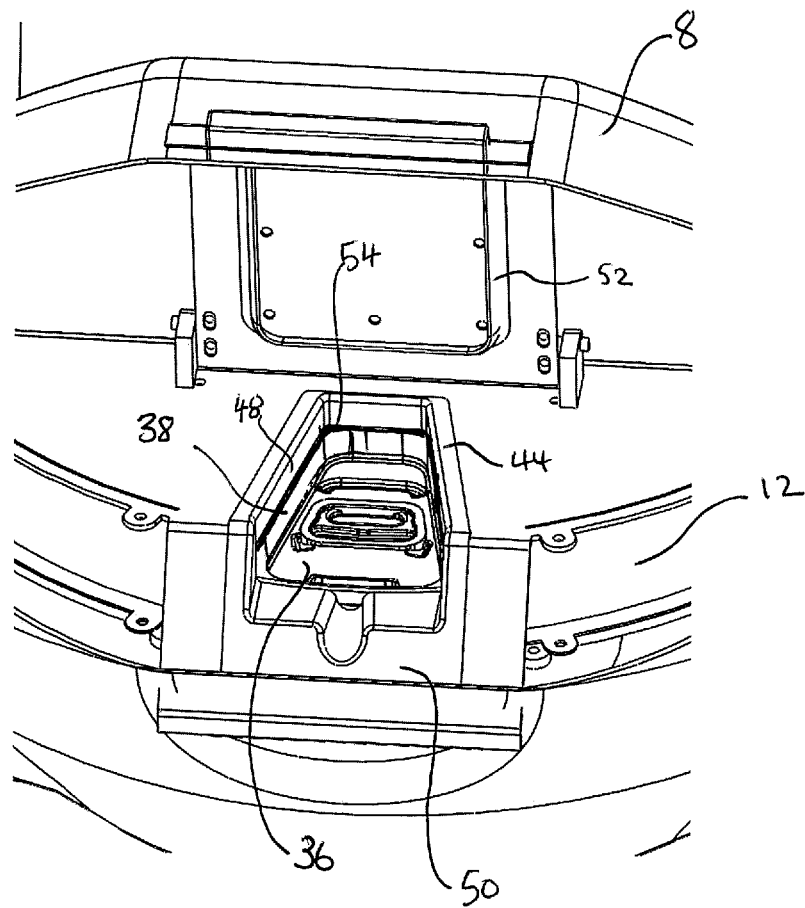
FIG. 7 schematically represents a close-up view of the loading port of the incubator apparatus of FIG. 1 with the loading port cover in an open position.
Figure 8:
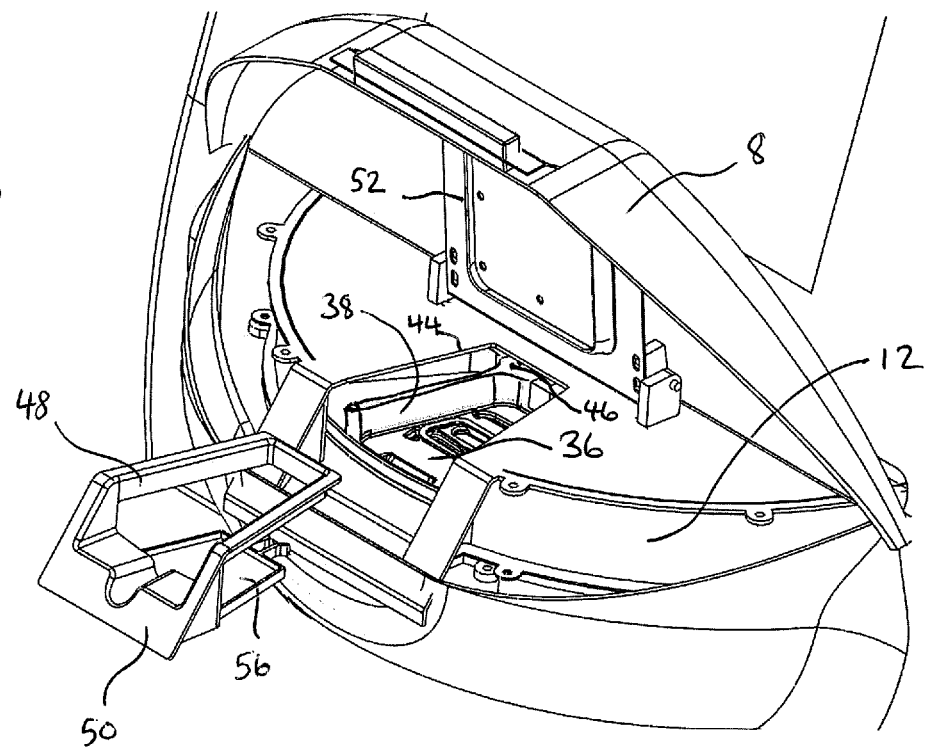
FIG. 8 schematically represents a close-up view of the loading port of the incubator apparatus of FIG. 1 with the loading port cover in an open position and the loading port insert detached.

In FIG. 1 the loading port 44 for (un)loading embryo slides 40 into compartments 36 of the slide carrier 14 is shown covered by the loading port cover 8. The loading port cover 8 is moveable so that it may be moved from a closed position in which the loading port cover prevents access to the loading port 44 from outside the apparatus, as seen in FIG. 1, to an open position in which the loading port 44 is exposed for access, as schematically represented in FIG. 6. Thus, FIG. 6 schematically represents in perspective view the front face of the apparatus represented in FIG. 1, but with the loading port cover 8 in the open position to allow loading/unloading of embryo slides into whichever compartment 36 is aligned with the loading port 44. FIGS. 7 and 8 are similar to FIG. 6 but show closer views of the region of the loading port 44 from different angles, and in the case of FIG. 8, with the loading port insert 50 represented separately from the incubation chamber housing 12. The loading port cover 8 is provided with a sealing ring 52, for example comprising a resilient material such as rubber or foam, arranged to help seal the loading port 44 from the surrounding atmosphere when the loading port cover 8 is in the closed position.

Operation of the loading port cover 8 may in some example embodiments be controlled by a locking system (not shown) which may be arranged to prevent accidental opening of the loading port cover 8. The loading port cover 8 may thus be locked in a closed position (the position schematically represented in FIG. 1) during normal operation, for examples during normal incubation when the motor 18 operates to rotate the slide carrier 14 to position embryos for image acquisition by the imaging system 20. The locking system may be configured so the loading port cover 8 may only be opened once the incubation programme, or user intervention through the user interface 6, has selected a particular slide for loading or unloading, the relevant compartment holding the selected slide has been rotated into alignment with the loading port 44 and the motor 18 has been switched off. Once the locking system releases the loading port cover 8, the loading port cover 8 may be opened so the relevant slide can be loaded or unloaded. When the loading port cover 8 is re-closed it may be automatically re-locked.

A potential issue with incubators is disturbance of the atmosphere within the incubation chamber during loading and unloading. As noted above, when incubating embryos it can be important to seek to maintain a stable environment, e.g. in terms of temperature and/or atmosphere, within the incubation chamber. However, loading or unloading embryos into the incubation chamber is one potential source of disturbance. In order to help reduce the extent to which the conditions within the incubation chamber are disturbed by the loading/unloading process in an apparatus in accordance with some embodiments of the invention the loading port wall 48 of the loading port and the compartment wall 38 of a compartment in the loading position are arranged to cooperate (align with one another) so as to restrict the extent to which the atmospheric environment of the compartment in the loading position (i.e. the volume of air in this compartment) is in fluid communication with the atmospheric environment of the other compartments which remain within the incubation chamber. Significantly, the atmospheric environments of the compartments that are not in the loading position (i.e. the other compartments in the incubation chamber) are in fluid communication and so share a common atmosphere. This is the case because it is the alignment of the loading port wall 48 and the compartment walls 38 which in effect separate the environment of the compartment in the loading position from its neighbouring compartments within the incubation chamber, but the atmospheric environments of the other compartments in the incubation chamber are in fluid communication (or specifically in the present context, in gas communication) because the atmosphere within the incubation chamber can move between them over the compartment walls 38. Thus the compartment in the loading position is separated from the other compartments in the incubation chamber by a separating wall provided by a combination of the loading port wall 48 and the compartment wall 38 for the compartment in the loading position. The respective walls are dimensioned and positioned so their respective edges (i.e. a bottom edge of the loading port wall 48 and an upper edge of the compartment wall 38 for the orientation represented in the figures) are brought into proximity as a selected compartment is moved to the loading position, as schematically seen in FIG. 7.

The size of the gap 54 that remains between the edges of the loading port wall and the compartment wall for the compartment in the loading position will determine the extent to which gas exchange between the compartment in the loading position and the other compartments is restricted. On the one hand the gap 54 should be made small to increase the blocking effect of the combined walls to separate the compartment in the loading position from the other compartments. On the other hand, if the walls 38, 48 are arranged so the gap 54 is very small there may be an increased risk of the respective walls jamming against one another. The size of the gap may thus be chosen taking account of the machining tolerances associated with the elements of the incubator apparatus.

In some embodiments an additional seal, for example a resilient strip (e.g. formed of rubber or nylon bristles, or a pneumatic tubing which can be inflated prior load door opening after a compartment selected for loading or unloading has been moved to the loading position), may be attached to the bottom edge of the loading port wall 48 to abut with the upper edge of a compartment wall in the loading position. Indeed, in another example the loading port wall 48 may itself comprise a resilient material, e.g. rubber, to allow for a small gap, or even no gap at all, between the loading port wall 48 and the compartment wall 38 of a compartment in the loading position with a reduced risk of jamming. Alternatively, or in addition, an upper edge of the compartment walls 38 (or the entire compartment walls 38) may similarly comprise a resilient/flexible material in some embodiments. In some example the size of any gap may be reduced, and in some instances eliminated, by arranging for the loading port wall 48 to be lowered and/or the compartment wall raised after the slide carrier has been rotated to the appropriate loading position and the motor stopped, but prior to load door opening. In a particular embodiment the loading port wall 48 may be lowered or the compartment wall raise so they touch to eliminating the gap entirely. Relative movement to bring the loading port and compartment walls together may be provided, for example, by raising the sample carrier (e.g. by moving the motor to which the slide carrier is attached along its rotation axis).

As noted above, slides carrying embryos are placed in compartments 36 defined by compartment walls during incubation. It is generally to be expected there will be some level of depression/profiling in the slide carrier to help receive and position the slides. In this regard it can be expected there will generally be at least some form of compartment wall between neighbouring slides. However, in principle a slide carrier in some examples may be entirely flat with slides simply being placed in desired positions on the flat surface and held in place in some other way, for example, by relying on friction, adhesive pads, or magnetics. In such a case the loading port wall may be adjustable to allow it to be changed from a closed configuration to an open configuration. In the closed configuration the loading port wall is in close proximity (or contact) with the slide carrier around the loading position to restrict gas exchange between the loading position and the atmosphere within the incubator. In the open configuration the loading port wall is spaced away from the slide carrier so as not to interfere with the movement of slides as they are rotated into and out of the loading position. The loading port wall may, for example, be configured to adopt the closed configuration before a loading port cover providing access to the loading position may be opened. In some examples the adjustment to allow movement from the closed configuration to the open configuration may be provided by the loading port wall having a component that is movable up and down in the manner of a shutter. In other examples the adjustment between the closed configuration in the open configuration may be provided by the loading port wall in effect comprising an expandable member, such as inflatable chamber/inflatable tubing, which may be expanded (e.g. inflated) to adopt the closed configuration and unexpanded (e.g. deflated) to adopt the open configuration as desired. In this regard there may be provided in accordance with some example implementations an incubator for embryos supported on embryo slides, the incubator comprising: an incubation chamber defined by an incubation chamber housing; and a slide carrier for holding embryo slides within the incubation chamber for incubation, wherein the slide carrier is moveable relative to the incubation chamber housing to allow a selected embryo slide to be moved to a loading position defined at least in part by a loading port wall associated with the incubation chamber housing, and wherein the loading port wall is changeable from a closed configuration to an open configuration, wherein in the closed configuration the loading port wall cooperates with the slide carrier around an embryo slide in the loading position to restrict the extent to which the environment of the embryo slide in the loading position is in fluid communication with the environments of other embryo slides in the incubation chamber, and in the open configuration the loading port wall is spaced away from the slide carrier to allow embryo slides to be moved into or out of the loading position.

There are various advantages associated with an incubator apparatus in accordance with the different aspects of the invention described herein.

For example in accordance with one aspect of the invention, the incubation chamber in some embodiments is generally disc-like with a slide carrier 14 being rotatable within the incubation chamber to allow a receptacle containing a selected embryo to be brought into alignment with the imaging device 20 for monitoring/image acquisition. This approach can provide a more compact design (e.g. greater capacity for a given apparatus footprint) than approaches based on linearly-translatable slide carriers. This is because a linearly-translatable slide carrier of a given size in effect needs a working space of around twice its size to bring both extremes of the slide carrier to a common monitoring position. In addition the arrangement of embryos on an arc of a circle centred on a rotation axis for the sample carrier can allow for relatively large numbers of embryos to be observed with movement in only one degree of freedom (rotation). This can simplify the construction of the device as compared to devices relying on XY-translatable stages.

Furthermore, the generally circular symmetry associated with a rotatable slide carrier can make it easier to maintain more uniform conditions in the different compartments than for a linearly-translatable slide carrier. For example, with a linearly-translatable slide carrier the regions at the end of the slide carrier may require special consideration, for example in terms of temperature control, because their immediate surroundings are different than for regions towards the middle of the slide carrier. Furthermore, slides placed towards the left side of a linear slide carrier will be moved to different positions within the instrument compared to those on the right side during incubation. With a circular slide carrier of the kind described above the immediate surroundings of the different compartments are broadly similar, and if the slide carrier is in effect continuously being rotated (i.e. as different embryos are sequentially aligned with the imaging device), the positions of all loaded slides will generally experience the same average environment and be similarly exposed to any positions within the incubator chamber that might potentially be subject to different conditions (e.g. in terms of temperature and/or gas composition).

In accordance with another aspect of the invention, in some embodiments the walls of the loading port and the walls of the compartments of the slide carrier cooperate to restrict the exchange of atmosphere between the incubation chamber and the external environment when the loading port cover 8 is open to help with maintaining stable incubation conditions in the incubation chamber. Furthermore, because the environments of the compartments which are not in the loading position are in fluid communication within the incubation chamber, a common incubation atmosphere is provided. This can help with reducing the extent of environment disturbance for embryos. For example, a newly-loaded embryo slide that is moved away from the loading position into the incubation chamber is exposed to a relatively large gas volume being maintained at the desired incubation conditions. This can allow the environment of the newly loaded embryos to more quickly align with the desired incubation conditions than would be the case if each embryo slide remained in a separately controlled compartment during incubation.

It will be appreciated that various embodiments of the invention may incorporate one or other or both of these two aspects. For example, in accordance with some embodiments an arrangement of cooperating walls as described above may be provided for a slight carrier which is linearly translatable rather than rotatable. In accordance with some other embodiments and arrangement of a rotatable slide carrier may be provided without using a cooperating wall arrangement.

It will further be appreciated the above-described example embodiments of the invention may be modified in various ways in accordance with other example embodiments of the invention.

For example, whereas the embryo slide 40 represented in FIG. 5 comprises receptacles arranged on a single arc of a circle, in another implementation an embryo slide may comprise receptacles arranged in groups on a number of different arcs of circles at different radii from the rotation axis 16 when the embryo slide is loaded it into a compartment of the sample carrier 14. For example, in addition to the receptacles 42 represented in FIG. 5, in accordance with some embodiments further receptacles may be provided along an arc which is closer to, or further from, the rotation axis 16 so as to in effect provide two (or more) lines of receptacles. In such a case the imaging device 20 may be arranged to have a sufficiently large field of view to image embryos in the different lines at the same time, or a drive mechanism may be provided to selectively move the imaging device 20 to different distances from the rotation axis 16 so that it may be aligned with the different arcs of receptacles. This latter approach introduces an additional drive mechanism to the apparatus to move the imaging device but can nonetheless be used to increase capacity, or provide a greater separation between receptacles for the same capacity, relative to an approach using a single arc of receptacles for holding embryos such as represented in FIG. 5. In yet another example a plurality of imaging devices with their respective imaging axes at different distances from the rotational axis may be provided (with corresponding viewing ports). Thus different imaging devices may image embryos in the arcs at different distances from the rotation axis.

Furthermore, whereas the incubation apparatus described above comprises a single monitoring position for image acquisition, in accordance with other embodiment of the invention further monitoring stations may be provided at other locations around the incubation chamber. For example, an additional imaging device may be provided to in effect double the rate at which images can be obtained. Alternatively, one or more additional monitoring stations for monitoring one or more different aspects of embryos being incubated may be provided. For example a station for monitoring gas respiration or any other parameter of interest may be provided at a different location around the incubation chamber at a distance from the rotation axis corresponding to the location of the embryos when in the incubator.

Thus apparatus and methods for monitoring embryos in an incubator are described. The apparatus comprises an incubation chamber defined by an incubation chamber housing and a slide carrier comprising a plurality of receptacles for holding embryos within the incubation chamber for incubation. The slide carrier may comprise a slide carrier on which embryo slides containing the receptacles may be placed during incubation. The slide carrier is rotatable about a rotation axis relative to the incubation chamber housing so as to allow receptacles to be selectively rotated to a monitoring position that is aligned with a viewing port provided in the incubation chamber housing, for example an opening or window. An imaging device is located outside the incubation chamber and arranged to image embryos within the incubation chamber at the monitoring position through the viewing port.

Further particular and preferred aspects of the present invention are set out in the accompanying independent and dependent claims. It will be appreciated that features of the dependent claims may be combined with features of the independent claims in combinations other than those explicitly set out in the claims.

What is claimed is:

1. An apparatus for monitoring embryos during incubation; the apparatus comprising:
    an incubation chamber defined by an incubation chamber housing;
    a sample platform comprising a plurality of receptacles for holding embryos within the incubation chamber for incubation, wherein the sample platform is rotatable about a rotation axis relative to the incubation chamber housing to allow embryos to be selectively rotated to a monitoring position aligned with a viewing port in the incubation chamber housing; and
    a lens located outside the incubation chamber and arranged to image embryos within the incubation chamber at the monitoring position through the viewing port, wherein the plurality of receptacles comprise a group of receptacles arranged to hold embryos at locations on an arc of a circle centered on the rotation axis and relative to the viewing port, wherein the sample platform comprises a slide carrier with a plurality of removable embryo slides containing the receptacles mounted thereon, wherein each embryo slide comprises a substrate with a plurality of receptacles provided therein, and wherein the receptacles are arranged at locations along an arc of a circle relative to the viewing port.

2. The apparatus of claim 1, wherein the plurality of receptacles comprise groups of receptacles arranged to hold embryos at locations on arcs of a plurality of circles centered on the rotation axis with different radii.

3. The apparatus of claim 2, wherein an imaging axis of the lens is moveable along a radial direction extending from the rotation axis to allow the imaging axis to be aligned with respective ones of the plurality of circles centered on the rotation axis with different radii.

4. The apparatus of claim 1, further comprising comprises imaging devices arranged on opposite sides of the incubation chamber.

5. The apparatus of claim 1, wherein the lens is part of a microscope.

6. The apparatus of claim 1, further comprising a motor for driving the rotation of the sample platform relative to the incubation chamber housing.

7. The apparatus of claim 6, further comprising a controller configured to control the motor to rotate a selected receptacle to the monitoring position.

8. The apparatus of claim 7, wherein the controller is configured to select a receptacle to be moved to the monitoring position in accordance with a predefined monitoring programme for embryos in the receptacles.

9. The apparatus of claim 1, wherein the slide carrier comprises a plurality of compartments for receiving embryo slides at locations corresponding to sectors around an arc of a circle centered on the rotation axis.

10. The apparatus of claim 9, wherein adjacent compartments are on either side of compartment walls extending in a radial direction away from the rotation axis.

11. The apparatus of claim 1, further comprising a temperature control circuit arranged to control a temperature of the sample platform.

12. The apparatus of claim 1, wherein the incubation chamber is gas controlled.

13. The apparatus of claim 1, further comprising monitoring equipment for monitoring an aspect of embryos in the incubation chamber, wherein the monitoring equipment is positioned such that the sample platform is rotatable about the rotation axis relative to the incubation chamber housing to allow embryos to be selectively rotated to a further monitoring position for monitoring by the monitoring equipment.

14. The apparatus of claim 1, wherein the sample platform is generally in the form of a circular disc.

15. The apparatus of claim 1, wherein the lens is arranged to view the embryos along a direction parallel to the rotation axis.

* * * * *